United States Patent [19]

Levin

[11] 4,103,175

[45] Jul. 25, 1978

[54] PHOTOTHERAPY IRRADIATION CHAMBER

[75] Inventor: Robert E. Levin, South Hamilton, Mass.

[73] Assignee: GTE Sylvania Incorporated, Danvers, Mass.

[21] Appl. No.: 743,873

[22] Filed: Nov. 22, 1976

[51] Int. Cl.² ............................................. G01J 1/00
[52] U.S. Cl. ..................................... 250/504; 250/503
[58] Field of Search ...................... 250/455, 503, 504; 128/371, 377; 313/489, 493

[56] References Cited

U.S. PATENT DOCUMENTS

| 834,755 | 10/1906 | Roberts | 128/377 |
|---|---|---|---|
| 1,583,420 | 5/1926 | Dicard | 128/371 |
| 1,796,134 | 3/1931 | Wörner | 128/371 |
| 2,504,576 | 4/1950 | Partlo et al. | 250/455 |
| 2,631,588 | 3/1953 | Paschell | 250/455 |

Primary Examiner—Alfred E. Smith
Assistant Examiner—B. C. Anderson
Attorney, Agent, or Firm—James Theodosopoulos

[57] ABSTRACT

A phototherapy irradiation chamber having substantial uniformity of irradiance therewithin comprises an array of vertical fluorescent lamps surrounding the irradiation space. Reflectors are located within the array at the top and bottom thereof. The ends of the lamps extend beyond the reflectors.

8 Claims, 6 Drawing Figures

PHOTOTHERAPY IRRADIATION CHAMBER

Phototherapy has long been used in the medical profession. Phototherapy is the irradiation of the human body, or portions thereof, with radiation in the optical spectrum, i.e. the ultraviolet, the visible, and the infrared regions of the electromagnetic spectrum. The ultraviolet region, in particular, has been used to induce photochemical, as opposed to thermal, effects. Use of ultraviolet alone has been reported as a treatment for many conditions, e.g., psoriasis, atopic eczema, neurodermatitis, etc. (Zimmerman, A.M.A. Arch. Derm. 78:646, 1958. A variety of ultraviolet ranges have been used for different purposes, e.g., UV-C (approx. 250-290 nm), UV-B (approx. 290-315 nm), and/or UV-A (approx. 315-400 nm).

A few conditions are known to be treatable by photochemotherapy, i.e. the combined use of drugs and radiation. The use of psoralen and the ultraviolet supplied in sunlight for vitiligo (a complete loss of pigment in a region ranging from small areas to the entire body) goes back many years in folk medicine and to 1948 (Kenney, Arch. Derm. 103:475, 1971) in modern medical practice. Psoriasis, a chronic epidermal proliferative disease, has been treated for half a century by the classic Goeckerman regime in which crude coal tar is applied topically and followed by exposure to UV-B.

In 1974 Parrish, Fitzpatrick, Tanenbaum, and Pathak (N.E.J. Med., 291:1207, 1974) reported a treatment for psoriasis in which orally administered methoxsalen is followed by exposure to UV-A. This protocol is very similar to one for treating vitiligo that was under simultaneous development by the same research group. This method of psoriasis treatment has many potential advantages over alternative methods; these advantages are well described in the standard medical literature. There are a variety of sources that generate ultraviolet, and several of these are well known and used in the medical field, such as fluorescent lamps with special phosphors, high pressure mercury discharge lamps, xenon discharge lamps, and carbon arcs. In terms of previous practice, none of these were satisfactory for this new photochemotherapy of psoriasis or for the similar treatment of vitiligo. The total body must be irradiated to energy density levels of up to about 30 or more joules/cm$^2$ of UV-A. The irradiance must be uniform on all parts of the body since the psoralen photosensitization causes a steep slope of the erythemadose curve. FIG. 1 shows the curve for the normal unsensitized human response to the normal tanning component of sunlight (UV-B) and to the psoralen sensitized response under UV-A exposure (PUVA). Since treatment requires an exposure above the level of detectable erythema, an increase of even 2:1 will cause severe burns, even though such an exposure change under normal sunlight experience would only increase the observed erythema slightly.

High pressure mercury discharge lamps (hot quartz lamps) would easily produce the required irradiance exposure level (watts/cm$^2$) to generate the required exposure dosage (joules/cm$^2$) in a practical length of time. However, such sources generate considerable UV-B and UV-C. These contribute to erythema and burn but not to the photochemical reaction required for treatment. Thus, the shorter wavelengths must be filtered out. The filtering can be difficult, and, more important, if the filters fail the potential human hazard is great. The sources operate at high surface temperatures (up to 900° C) with the associated hazards unless the patient is well protected. Most important, with such physically small sources, it would be extremely difficult in any practical system to provide uniform irradiance over the total three dimensional human body. Finally, the conversion efficiency of these lamps to the UV-A is on the order of 5 to 10 percent, resulting in a large heat load on the patient. In fact, infrared filtering and special cooling techniques would be required if such a source were to be used to its full potential for high irradiance and if a patient were to tolerate exposure for the required time.

Solar UV-A is inadequate for many reasons. Total body exposure is required. Uniform exposure would require carefully controlled rotation of the patient. In many parts of the world sunlight is not available much of the time. Finally, exposures lasting several hours would be required even at the southernmost latitudes in this country. Solar UV-A is impractical both in terms of required patient time and from the fact that the psoralen-induced response is only consistent and controllable for slightly over an hour interval.

Fluorescent lamps are an ideal source for this application. Their conversion efficiency to the UV-A can be as high as 25-30 percent, one of the highest attainable, thus limiting the heat load on the patient while minimizing the required exposure time by operating at a high irradiance level. With these sources the patient generally is close to his tolerance limit on heat, indicating that all other sources will cause problems in this direction. The sources operate at low temperature (on the order of 40° C) and consequently do not present a contact burn hazard. The posphor can be designed to radiate principally in the UV-A, eliminating the need to filter the shorter wavelength ultraviolet radiation. Finally, the sources are physically large low power density sources thereby making it possible to meet the design requirement of uniform irradiance.

There have been many attempts in the medical field to use fluorescent lamps as the source of UV-A exposure (principally with black light lamps), and some of these have been successful when the required exposure level is low. However, it was generally thought that the fluorescent lamp could not produce adequately high levels for practical application in the orally activated psoriasis treatment or in the treatment of vitiligo by similar protocol. Schafer states (*The Biologic Effects of Ultraviolet Radiation*, F. Urbach, editor, Pergamon Press, 1969, page 70) with regard to the low pressure mercury lamp: "It is possible to coat such a low-pressure lamp with a fluorescent substance in order to obtain a continuous or almost continuous spectrum which includes the ultraviolet range. Fluorescent lamps which are designed on this principle are well-known in illumination engineering. The specific efficiency and radiance of such lamps is very low. High-radiant intensities, and above all, high local radiant intensities are, however, difficult to produce with fluorescent lamps because of their large dimensions."

It was often stated that sources specifically emitting in the UV-A were unacceptable for medical applications. For example, Becker (Becker, J.A.M.A. 202:422, 1967) states: "All of the psoralens sensitize the skin in the area of 360 mu. There is no ideal light source for this wavelength." It was not unusual in the medical field for other investigators to reach this conclusion that fluorescent type lamps are completely inadequate for photochemotherapy. For example, Africk and Fulton (Africk and Fulton, Br. J. Derm. 84:151, 1971) tried black light type lamps in the treatment of vitiligo and concluded: "Since none of the patients had shown evidence of marked erythema or repigmentation, the light source was then changed to natural sunlight between the hours of 11 a.m. and 3 p.m." However, with some designs of irradiation systems, certain treatments in the area of photochemotherapy were successful using black light lamps. These generally were those processes requiring only low levels of UV-A. Cylindrical irradiation chambers to enclose patients were thus used in the medical field previously. Representative of prior art chambers is a unit described by Weber (Weber, Br. J. Derm., 90:317, 1974) which produces a UV-A irradiance level on the order of 0.5 milliwatts/$cm^2$ with greater than 2:1 variation in irradiance within the chamber. This level is more than an order of magnitude too low for the present requirements, and the uniformity is completely unacceptable.

I have found that fluorescent lamps can be used in irradiation chambers to achieve the 10 milliwatts/$cm^2$ and above of UV-A necessary for photochemotherapy with reasonable patient exposure times while at the same time achieving considerable improvement in radiance uniformity within the chamber. The general construction of such a chamber is shown in copending application Ser. No. 693,029, filed June 4, 1976 entitled "Modular Photochemotherapy Chamber," the disclosure of which is incorporated herein by reference. The instant application is more particularly concerned with the optics of such a chamber necessary for attainment of the above mentioned results.

In the drawings, FIG. 1 shows a curve for the normal unsensitized human response to the normal tanning component of sunlight (UV-B) and another curve for the psoralen-sensitized response under UV-A exposure (PUVA).

Figure 3:
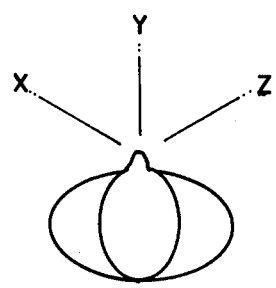
FIG. 3 is a diagrammatic representation of the plan view of a patient showing radiation from different directions striking the patient's face.

A prime requirement of the optical system is that any small plane element within the volume space of the chamber shall receive radiant power through $2\pi$ steradians, i.e. from all directions within a hemispherical zone. In this way the irradiance will be uniform on all such elements wherever they are located or however they are spatially oriented. It is not adequate to use a source which is far away and rely on a constant distance in the inverse square law as is often suggested. FIG. 3, which is a top view of a patient, shows the reason. Even though a region of the face may be at a constant distance from a source, radiation at points X, Y and Z cannot be the same due to the different spatial orientations of the surfaces. This condition of a ubiquitous source is fulfilled when essentially the entire cylindrical surface is formed of fluorescent lamps. If significant space is left between the lamps, then a loss proportional to this spacing fraction will occur. It would seem that the loss can be reduced by placing reflectors in the voids. However, then the irradiance provided within the chamber has a strong component of multiply reflected radiant flux across the chamber. Consequently, the irradiance will be a function of the patient's body size and location. Further, reflectors are functional in producing a ubiquitous source only if the lamps adjacent to the reflector contribute flux to that reflector. This is not possible with reflector type fluorescent lamps. Since reflector lamps inherently have a higher radiant exitance than nonreflector lamps for any choice of phosphor, lamp loading, etc., then the reflector lamps in an essentially continuous array produce the highest possible irradiance on patients in the chamber.

Figure 4:
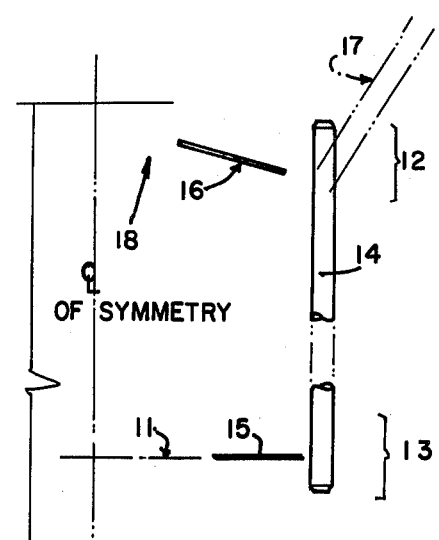
FIG. 4 and FIG. 5 are partial sectional views through the center line of the chamber.
Figure 5:
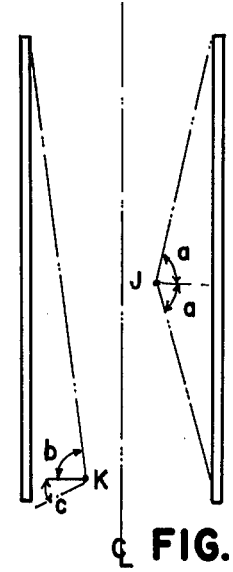

All prior systems lacked uniform irradiance within the chamber. If a cylindrical array of lamps is formed, symmetrical uniformity at any cylindrical cross section will occur automatically. However, uniformity along the axial direction of the cylinder does not occur. All previous systems were deficient in this specific respect. FIG. 4 illustrates the two step solution. A patient stands on platform mat 11. The two ends 12 and 13 of each fluorescent lamp 14 are located outside of the active system since the radiant exitance of these cathode regions is known to be low. This low exitance compounds the effect caused by the fact that in the central region in the axial direction a target element receives radiation from both ends while near an end radiation is received principally from one side. This is schematically illustrated in FIG. 5 for a cylindrical source array. At point J, radiation is received through ± angle a. At point K, radiation is received from one side through angle b which is essentially equal to angle a. From the other side, radiation is received through angle c which is small. Consequently, the irradiance at point J is approximately twice that at K.

Controlling the basic end loss is the second step in the solution. This is done with reflectors 15 and 16 (FIG. 4) which provide virtual images of lamp 14 such that the upper and lower extremities of the patient receive radiation essentially through $2\pi$ steradians. Reflector 16 is inclined so that the virtual lamp image 17 seen through the clear aperature of reflector 16 contributes maximally at the head. A flat reflector would not do this since region 18 is left open to permit head clearance and provide a location for flow of ventilating air.

Figure 1:
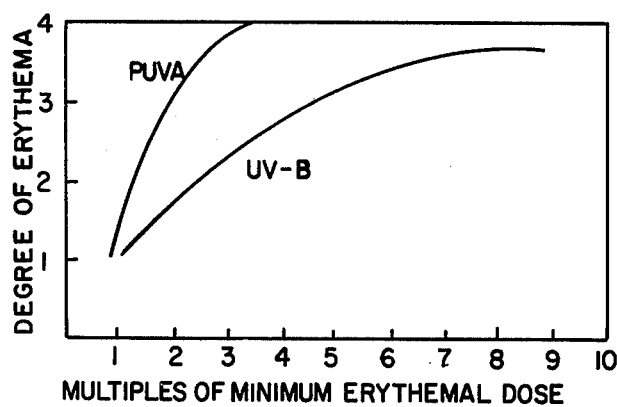
Figure 2:
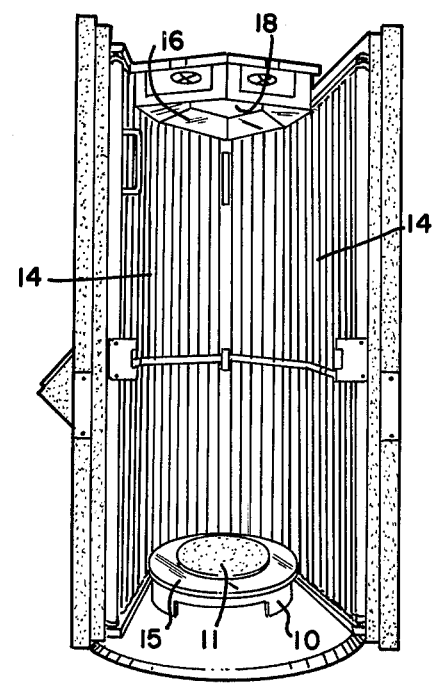
FIG. 2 is a perspective view of the interior of a chamber in accordance with this invention.

In an irradiation chamber in accordance with this invention, shown in FIG. 2, there is a raised platform 10 which is several inches above the lower ends of lamps 14. The patient stands on a circular mat 11 surrounded by larger diameter lower reflector 15 which is on the upper surface of platform 10. Reflector 16 at the top of the chamber is several inches below the tops of lamps 14. Reflector 16 comprises a plurality of individual panels, each of which is inclined as shown in FIG. 4, disposed around central region 18 left open for ventilation purposes. There is an array of vertical fluorescent lamps 14 surrounding the irradiation space. In a specific embodiment, the cross-sectional shape of the chamber was a regular hexagon. There were ten vertical lamps on each of five sides of the hexagon and only nine on the sixth side thereby permitting a narrow vertical opening 19 for a viewing port through which the patient is observed. Each lamp was a T12, 69 watt, 235° internal reflector, 83 inch length, used the Sylvania #2011 phosphor and was enclosed in a 30 mil thick cylindrical substantially transparent protective sleeve. The lamp center spacing was 1 13/16 inch and the outer diameter of each lamp sleeve was 1.64 inch.

The free area within the chamber is defined by a regular hexagon tangent to the lamp surfaces and was 795 square inches. Bottom reflector 15 was an annular ring 28 inches outer diameter by 17 inches inner diameter and had a reflector area of 389 square inches, which is 49% of the free cross section area. Top reflector 16 consisted of six isosceles trapezoidal sections each of which was inclined about 15° from the horizontal. The total reflector area was 515 square inches, had a projected area on a horizontal plane of 497 square inches and occupied 62½% of the free area of the chamber. The reflectors were anodized specular aluminum reflector sheets, having a total hemispherical reflectance of at least 0.85 within the system functional UV-A band.

Figure 6:
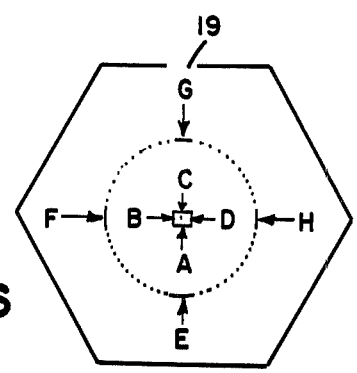
FIG. 6 is a diagram showing the locations at which the irradiance was measured within the chamber.

The uniformity of irradiance within the chamber can be shown by measurements made at the positions shown in FIG. 6. Positions A, B, C and D are at the chamber centerline and represent four vertical surfaces 90° apart. Positions E, F, G and H represent four vertical surfaces parallel to A, B, C and D respectively, but displaced 8 inches from the centerline outward toward the walls of the chamber. At all positions the measurements were made with the photometer facing outwards. Table I shows the irradiance in milliwatts per square centimeter of the 320–380 nm radiation at the eight positions for each of five planes located 8, 24, 40, 56 and 72 inches, respectively, above platform 10.

TABLE I

| Vertical Irradiance Plane | Irradiance in milliwatts per square centimeter. Height above platform, inches | | | | |
|---|---|---|---|---|---|
| | 8 | 24 | 40 | 56 | 72 |
| A | 13.2 | 15.5 | 16.0 | 16.3 | 14.0 |
| B | 14.5 | 17.0 | 17.5 | 17.8 | 15.0 |
| C | 14.5 | 17.8 | 18.0 | 18.0 | 15.0 |
| D | 13.5 | 16.5 | 17.2 | 17.0 | 14.5 |
| E | 12.9 | 15.7 | 16.2 | 16.5 | 14.7 |
| F | 14.5 | 16.8 | 17.7 | 18.0 | 15.6 |
| G | 15.2 | 17.6 | 18.5 | 18.9 | 16.1 |
| H | 14.4 | 16.7 | 17.0 | 17.3 | 14.8 |

It can be seen that there is substantial uniformity within the chamber and that all measurements are within plus or minus 25% of the average measurement of 16.1 milliwatts per square centimeter.

I claim:

1. A phototherapy irradiation chamber having substantial uniformity of irradiance of 320–380 nanometer radiation therewithin comprising an array of vertical fluorescent lamps surrounding the irradiation space, a bottom reflector and a top reflector disposed within the array at the bottom and top respectively of the irradiation space, the ends of the lamps extending beyond the reflectors for the purpose of obtaining said substantial uniformity of irradiance.

2. The chamber of claim 1 wherein the irradiance at substantially all points within the irradiation space is above about 10 milliwatts per square centimeter.

3. The chamber of claim 1 wherein the irradiance at substantially all points within the irradiation space is within about plus or minus 25% of the average irradiance value within said space.

4. The chamber of claim 1 wherein the bottom reflector is in the shape of an annular ring and is perpendicular to the axis of the irradiation space.

5. The chamber of claim 1 wherein the lower cathode regions of the lamps are below the bottom reflector.

6. The chamber of claim 1 wherein the top reflector comprises a plurality of individual reflector sections disposed around a central ventilating opening and each reflector section is shallowly inclined with respect to the horizontal.

7. The chamber of claim 1 wherein the upper cathode regions of the lamps are above the top reflector.

8. The chamber of claim 1 wherein the area of each reflector is a substantial fraction of the free area within the chamber.

* * * * *